(12) United States Patent  
Soerens et al.

(10) Patent No.: US 7,115,321 B2
(45) Date of Patent: Oct. 3, 2006

(54) ABSORBENT BINDER COATING

(75) Inventors: Dave Allen Soerens, Neenah, WI (US); Julie Anne Draves, Bixby, OK (US); Lawrence Howell Sawyer, Neenah, WI (US); Jason Matthew Laumer, Appleton, WI (US); Shannon Kathleen Melius, Appleton, WI (US); Debra Jean McDowall, Neenah, WI (US); Rob D. Everett, Appleton, WI (US); Henry L. Griesbach, III, Clarkston, GA (US); Brenda Marie Nelson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 143 days.

(21) Appl. No.: 10/427,700

(22) Filed: May 1, 2003

(65) Prior Publication Data

US 2004/0043688 A1    Mar. 4, 2004

Related U.S. Application Data

(63) Continuation-in-part of application No. 10/324,478, filed on Dec. 20, 2002, now Pat. No. 6,849,685, and a continuation-in-part of application No. 10/206,883, filed on Jul. 26, 2002, now Pat. No. 6,737,491.

(51) Int. Cl.
  *B32B 27/30* (2006.01)
(52) U.S. Cl. ............ 428/500; 428/913; 442/118; 442/119; 442/149; 442/154; 442/156; 442/157; 525/309; 526/279; 526/320
(58) Field of Classification Search .......... 428/105, 428/122, 913; 442/118, 119, 149, 154, 156, 442/157; 526/271, 277, 279, 287, 317.1, 526/32, 320
See application file for complete search history.

(56) References Cited

U.S. PATENT DOCUMENTS

| 3,617,362 A | 11/1971 | Bemmels et al. |
| 3,951,893 A | 4/1976 | Gander |
| 3,959,242 A | 5/1976 | Watts et al. |
| 3,963,605 A | 6/1976 | Seabourn |
| 3,963,805 A | 6/1976 | Chu |
| 4,251,643 A | 2/1981 | Harada et al. |
| 4,291,136 A | 9/1981 | Keogh |

(Continued)

FOREIGN PATENT DOCUMENTS

CA    756190    4/1967

(Continued)

OTHER PUBLICATIONS

American Society for Testing Materials (ASTM) Designation: D1003-00, "Standard Test Method for Haze and Luminous Transmittance of Transparent Plastics," pp. 1-6, Published Jul. 2000.

(Continued)

*Primary Examiner*—Helen L. Pezzuto
(74) *Attorney, Agent, or Firm*—Pauley Petersen & Erickson (57) ABSTRACT

An absorbent binder coating including monoethylenically unsaturated polymer units, polyacrylate ester units that include an alkoxysilane functionality, and polyolefin glycol units and/or polyolefin oxide units, can be applied to various substrates. For example, the coating can be self-applied to an article of clothing or to a person's skin to provide absorbency. Alternatively, the coating can provide moisture absorbency, as well as adhesive properties, when incorporated into various articles including medical devices, wound dressings, laminates, absorbent garments, packaging materials, and horticultural products.

33 Claims, 7 Drawing Sheets

U.S. PATENT DOCUMENTS

| | | | |
|---|---|---|---|
| 4,328,323 A | 5/1982 | Keogh | |
| 4,343,917 A | 8/1982 | Keogh | |
| 4,353,997 A | 10/1982 | Keogh | |
| 4,369,289 A | 1/1983 | Keogh | |
| 4,408,011 A | 10/1983 | Barnabeo | |
| 4,434,272 A | 2/1984 | Keogh | |
| 4,440,907 A | 4/1984 | Keogh | |
| 4,446,279 A | 5/1984 | Keogh | |
| 4,459,396 A | 7/1984 | Yamasaki et al. | |
| 4,489,029 A | 12/1984 | Keogh et al. | |
| 4,493,924 A | 1/1985 | Rifi | |
| 4,502,968 A | 3/1985 | Noda et al. | |
| 4,526,930 A | 7/1985 | Keogh | |
| 4,551,504 A | 11/1985 | Barnabeo | |
| 4,575,535 A | 3/1986 | Keogh | |
| 4,579,913 A | 4/1986 | Keogh | |
| 4,589,876 A | 5/1986 | Van Tilburg | |
| 4,593,071 A | 6/1986 | Keogh | |
| 4,676,820 A | 6/1987 | Le Sergent et al. | |
| 4,753,993 A | 6/1988 | Keogh | |
| 4,767,820 A | 8/1988 | Keogh | |
| 4,806,594 A | 2/1989 | Gross et al. | |
| 4,921,136 A | 5/1990 | Roggenburg, Jr. | |
| 4,940,646 A | 7/1990 | Pawlowski | |
| 5,047,476 A | 9/1991 | Keogh | |
| 5,089,564 A | 2/1992 | Bullen | |
| 5,112,919 A | 5/1992 | Furrer et al. | |
| 5,145,906 A | 9/1992 | Chambers et al. | |
| 5,196,470 A | 3/1993 | Anderson et al. | |
| 5,204,404 A | 4/1993 | Werner, Jr. et al. | |
| 5,354,829 A | 10/1994 | Swisher et al. | |
| 5,364,382 A | 11/1994 | Latimer et al. | |
| 5,389,728 A | 2/1995 | Prejean | |
| 5,532,350 A | 7/1996 | Cottrell et al. | |
| 5,656,132 A | 8/1997 | Farrington, Jr. et al. | |
| 5,853,867 A | 12/1998 | Harada et al. | |
| 5,859,074 A | 1/1999 | Rezai et al. | |
| 5,911,937 A | 6/1999 | Hekal | |
| 5,932,668 A | 8/1999 | Friebe et al. | |
| 5,945,476 A | 8/1999 | Roesler et al. | |
| 5,961,763 A | 10/1999 | Makoui et al. | |
| 6,013,855 A | 1/2000 | McPherson et al. | |
| 6,020,071 A | 2/2000 | Watson | |
| 6,020,171 A | 2/2000 | Saito et al. | |
| 6,054,523 A | 4/2000 | Braun et al. | |
| 6,110,533 A | 8/2000 | Cote et al. | |
| 6,183,872 B1 | 2/2001 | Tanaka et al. | |
| 6,200,684 B1 | 3/2001 | Yamaguchi et al. | |
| 6,214,274 B1 | 4/2001 | Melius et al. | |
| 6,300,275 B1 | 10/2001 | Weir | |
| 6,315,765 B1 | 11/2001 | Datta et al. | |
| 6,380,298 B1 | 4/2002 | Flautt et al. | |
| 6,387,084 B1 | 5/2002 | VanGompel et al. | |
| 6,403,857 B1 | 6/2002 | Gross et al. | |
| 6,417,425 B1 | 7/2002 | Whitmore et al. | |
| 6,458,877 B1 | 10/2002 | Ahmed et al. | |
| 6,464,675 B1 | 10/2002 | De Carvalho | |
| 6,497,690 B1 | 12/2002 | Haarer | |
| 6,534,572 B1 | 3/2003 | Ahmed et al. | |
| 6,596,402 B1 | 7/2003 | Soerens et al. | |
| 6,689,934 B1 | 2/2004 | Dodge et al. | |
| 6,737,491 B1 | 5/2004 | Soerens et al. | |
| 6,808,801 B1 | 10/2004 | George et al. | |
| 6,822,135 B1 | 11/2004 | Soerens et al. | |
| 6,849,685 B1 | 2/2005 | Soerens et al. | |
| 6,887,961 B1 | 5/2005 | Soerens et al. | |
| 6,964,803 B1 | 11/2005 | Krautkramer et al. | |
| 2002/0049417 A1 | 4/2002 | Onishi et al. | |
| 2002/0090453 A1 | 7/2002 | Muthiah et al. | |
| 2003/0008989 A1* | 1/2003 | Gore et al. | |
| 2003/0100875 A1 | 5/2003 | Suekane et al. | |
| 2003/0149413 A1 | 8/2003 | Mehawej | |
| 2004/0019339 A1 | 1/2004 | Ranganathan et al. | |
| 2004/0043688 A1 | 3/2004 | Soerena et al. | |
| 2004/0106721 A1 | 6/2004 | Soerens | |
| 2004/0116014 A1 | 6/2004 | Soerens et al. | |
| 2004/0116885 A1 | 6/2004 | Soerens et al. | |
| 2004/0122390 A1 | 6/2004 | Soerens et al. | |

FOREIGN PATENT DOCUMENTS

| | | |
|---|---|---|
| EP | 0 132 910 A2 | 2/1985 |
| EP | 0 475 664 A1 | 3/1992 |
| EP | 0 705 861 A1 | 4/1996 |
| EP | 0 844 265 A1 | 5/1998 |
| EP | 0 992 252 | 4/2000 |
| EP | 1 013 291 A1 | 6/2000 |
| EP | 1 059 320 A2 | 12/2000 |
| EP | 1 138 293 A1 | 10/2001 |
| EP | 1 199 059 | 4/2002 |
| EP | 1 529 506 A2 | 5/2005 |
| WO | 99/57201 | 11/1999 |
| WO | WO 02/053664 A2 | 7/2002 |

OTHER PUBLICATIONS

Neumann, A.W., and R.J. Good, "Techniques of Measuring Contact Angles," Chapter 2, Surface and Colloid Science—Experimental Methods, vol. 11, edited by R.J. Good and R.R. Stromberg, Plenum Press, 1979, pp. 31-91.

* cited by examiner

ABSORBENT BINDER COATING

RELATED APPLICATIONS

This application is a continuation-in-part of U.S. patent application Ser. No. 10/206,883, filed on 26 Jul. 2002, now U.S. Pat. No. 6,737,491 the disclosure of which is incorporated by reference. This application is also a continuation-in-part of U.S. patent application Ser. No. 10/324,478, filed 20 Dec. 2002, now U.S. Pat. No. 6,849,685 the disclosure of which is incorporated by reference.

BACKGROUND OF THE INVENTION

This invention is directed to a combination of an absorbent binder coating and various substrates to which the coating is applied.

A number of products that are exposed to moisture or humidity during use often lack absorbent properties because of impracticalities. More particularly, it may seem impractical to apply an absorbent layer of material to a surface because absorbent materials are often bulky, thus there may not be any perceptible space on the article to which absorbent material may be attached without getting in the way. Furthermore, the cost of adding absorbent material may be prohibitively expensive. Additionally, it may be difficult to find a binder material that can attach the absorbent material to the article without damaging the article.

While adhesives beneficially hold products together, such as adhering an absorbent material to a product, adhesives may also have a tendency to interfere with the absorbency of fluids in adhesively attached absorbent materials. Adhesives are typically hydrophobic and therefore are not conducive to absorbency or liquid transfer functions. Furthermore, most adhesives are non-absorbent and thus serve no liquid retention function.

Hydrophilic adhesives are known, such as adhesives formulated from water-soluble polymers such as poly(vinyl alcohol), poly(vinyl methyl ether), poly(vinyl pyrrolidone), poly(ethylene oxide), or cellulose derivatives such as hydroxypropyl cellulose. Dextrans, starches and vegetable gums have been used to provide hydrophilic adhesives. These materials provide adhesion under dry conditions. However, upon exposure to aqueous fluids, these materials lose bonding capability because they are substantially soluble in aqueous fluids.

A known approach for making hydrophilic adhesives more functional upon exposure to aqueous fluid is to crosslink the water-soluble polymers. As a result of crosslinking, the material becomes swellable, and no longer soluble, in aqueous fluid. However, crosslinked polymers are difficult to apply to substrates or to establish intimate contact with surfaces because the crosslinked polymers are solid materials and have little or no ability to flow. Some crosslinked materials are fairly stiff, and inhibit the flexibility of the absorbent product.

What is therefore needed is a hydrophilic binder or coating that has latent crosslinking capability and which can be produced at an attractive cost. Such binder or coating could be easily applied to various surfaces, since the hydrophilic binder or coating would be capable of flow prior to crosslinking. Latent crosslinking capability would also provide a simple means of crosslinking the polymer after the polymer has established intimate contact with substrates or has formed a desired final shape or form.

Post-application crosslinking techniques are well known. Typical means of inducing the formation of crosslinks include high temperature "curing" or exposure to radiation, such as ultraviolet or gamma radiation. Another known means of post-application crosslinking is moisture-induced crosslinking.

Recent development efforts have provided coating materials for a variety of uses. For example, U.S. Pat. No. 6,054,523, to Braun et al., describes materials that are formed from organopolysiloxanes containing groups that are capable of condensation, a condensation catalyst, an organopolysiloxane resin, a compound containing a basic nitrogen, and polyvinyl alcohol. The materials are reported to be suitable for use as hydrophobic coatings and for paints and sealing coatings.

Anderson et al., in U.S. Pat. No. 5,196,470, reported an alcohol-based, water-soluble binder composition. Because this composition is water-soluble and not cross-linked, it has no absorbency.

Others have reported the production of graft copolymers having silane functional groups that permitted the initiation of cross-linking by exposure to moisture. Prejean (U.S. Pat. No. 5,389,728) describes a melt-processable, moisture-curable graft copolymer that was the reaction product of ethylene, a 1–8 carbon alkyl acrylate or methacrylate, a glycidyl containing monomer such as glycidyl acrylate or methacrylate, onto which has been grafted N-tert-butylaminopropyl trimethoxysilane. The resulting copolymers were reported to be useful as adhesives and for wire and cable coatings.

Furrer et al., in U.S. Pat. No. 5,112,919, reported a moisture-crosslinkable polymer that was produced by blending a thermoplastic base polymer, such as polyethylene, or a copolymer of ethylene, with 1-butene, 1-hexene, 1-octene, or the like; a solid carrier polymer, such as ethylene vinylacetate copolymer (EVA), containing a silane, such as vinyltrimethoxysilane; and a free-radical generator, such as an organic peroxide; and heating the mixture. The copolymers could then be cross-linked by reaction in the presence of water and a catalyst, such as dibutyltin dilaurate, or stannous octoate.

U.S. Pat. No. 4,593,071 to Keough reported moisture cross-linkable ethylene copolymers having pendant silane acryloxy groups. The resultant cross-linked polymers were reported to be especially resistant to moisture and to be useful for extruded coatings around wires and cables. The same group has reported similar moisture curable polymers involving silanes in U.S. Pat. Nos. 5,047,476, 4,767,820, 4,753,993, 4,579,913, 4,575,535, 4,551,504, 4,526,930, 4,493,924, 4,489,029, 4,446,279, 4,440,907, 4,434,272, 4,408,011, 4,369,289, 4,353,997, 4,343,917, 4,328,323, and 4,291,136.

U.S. Pat. No. 5,204,404 to Werner reported crosslinkable hydrophobic acrylate ester copolymers including 0.1 to 10% acrylic acid. The resultant cross-linked polymers were reported to be useful for painting and refinishing the exterior of automobiles.

These examples of moisture-induced crosslinking are applied to substantially hydrophobic polymers. Since the cured products of these formulations are reported to be useful for coverings for non-conductive coatings for electrical conductors, and for painting and refinishing the exterior of automobiles, it would be expected that they are durable coatings for which properties such as water absorbency would be a disadvantage.

There is thus a need or desire for a multi-purpose absorbent crosslinkable binder coating that can be applied to a variety of articles to create an absorbent coating that is thin, durable, cost efficient, non-obtrusive, and possibly removable.

SUMMARY OF THE INVENTION

This invention is directed to a combination of a crosslinkable absorbent binder coating applied to various substrates. The absorbent binder coating includes a hydrophilic polymer which is capable of post-application, moisture-induced crosslinking, is durable, relatively inexpensive to produce, and can be removed from surfaces and discarded after use.

The crosslinkable absorbent binder coating can be directly applied to a person's skin, or to an article of clothing, or other suitable substrate. After use, the absorbent binder coating can be removed and discarded. Alternatively, a mesh layer may be placed between the substrate and the absorbent binder coating to facilitate removal of the absorbent binder coating after use. The absorbent binder coating may include a fragrance additive, odor-absorbing particles, and/or an antimicrobial additive to provide additional benefits.

Other substrates to which the absorbent binder coating may be applied include a mirror, camera lens, electronic display, or other types of surfaces that may be subjected to moist or humid conditions. The absorbent binder coating would absorb such moisture and thereby prevent fogging or other moisture-related occlusion of display surfaces. Other articles to which the absorbent binder coating may be applied include personal care absorbent garments, with the coating applied to a waistband or side panels to absorb moisture. A number of medical devices could also benefit from the application of the absorbent binder coating, including catheters and guide wires, as well as wound dressings.

In addition to providing absorbency and the ability to attach itself to substrates without the need for an additional binder, the absorbent binder coating can also be used to bond one layer to another. For example, the absorbent binder coating may bond a liquid-permeable layer to a liquid-impermeable layer, thereby providing some absorbency between the two layers, such as in an absorbent garment, or in a mattress pad.

Another application in which the absorbent binder coating can be used is in packaging material. For example, the absorbent binder coating can be applied to food storage containers, such as carry-out boxes, or produce storage bags, or shipping containers, to absorb excess moisture from the contents within the packaging as well as to release controlled water vapor to maintain optimum humidity.

Yet another application in which the absorbent binder coating can be used is in horticultural products. More particularly, the absorbent binder coating can include one or more additives, such as fertilizer, auxin, fungicide, and/or floral preservative, and can be used to coat seeds or fertilizer pellets. Additionally, seeds or fertilizer pellets coated with the absorbent binder coating may be applied to a fabric, tape, or other substrate to provide for automated planting. The absorbent binder coating, with one or more additives, may be applied to plant cuttings for plant propagation or for cut flower preservation.

The absorbent binder coating includes about 15–99.8% by mass of monoethylenically unsaturated polymer units. Suitable monoethylenically unsaturated polymers include without limitation carboxylic acid, sulphonic acid, phosphonic acid, and salts of the foregoing. The absorbent binder coating also includes about 0.1–20% by mass of acrylate or methacrylate ester units that include an alkoxysilane functionality. Upon exposure to water, the alkoxysilane functionality forms a silanol group which condenses to form a crosslinked polymer.

The absorbent binder coating also includes about 0.1–75% by mass of polyolefin glycol and/or polyolefin oxide units. The polyolefin glycol and/or oxide may include an alpha-olefin having about 2–4 carbon atoms, and may include about 30–15,000 olefin glycol and/or oxide units per molecule. The polyolefin glycol may be a homopolymer or copolymer, including block copolymer of an olefin glycol of a different number of carbon atoms. For example, block copolymers of ethylene oxide and propylene oxide. The polyolefin glycol and/or oxide may be graft polymerized with the acrylate or methacrylate ester to form a graft copolymer. The polyolefin glycol and/or oxide provides the absorbent binder coating with enhanced flexibility. Thus, the absorbent binder coating has enhanced adhesion in a wet condition, absorbency, and flexibility.

The absorbent binder coating can be prepared using a template polymerization process by which the monoethylenically unsaturated polymer and acrylate or methacrylate ester are polymerized in the presence of a pre-formed template polymer, which is the polyolefin glycol and/or polyolefin oxide. The polymerization can be carried out by reacting two different monoethylenically unsaturated monomers, one of which contains an alkoxysilane functionality. The polymerization may be induced by heat, radiation, redox chemical reactions, and other techniques. Suitable radiation initiators include without limitation ultraviolet, microwave, and electron beam radiation. The initiator generates free radicals to cause copolymerization of the monomers. In one embodiment, the polymerization reaction is carried out in an organic solvent such as ethanol. The polymerization may also occur in an aqueous solution, or in a combined aqueous and organic solvent.

The polyolefin glycol and/or oxide may or may not be graft polymerized onto the acrylate or methacrylate units during the polymerization process. The resulting absorbent binder coating may contain the polyolefin glycol and/or oxide as a separate component, or as part of the copolymer, or a combination of both.

The resulting polymer has latent moisture-induced crosslinking capability due to the alkoxysilane functionality. This polymer may be applied, in a flowable state, to a substrate or other end use application. Moisture-induced crosslinking may be accomplished through hydrolysis of the alkoxysilane and subsequent condensation upon removal of the solvent from the substrate, either by evaporation of the solvent from the substrate or using any other effective technique. Alternatively, the hydrolysis of the alkoxysilane and subsequent condensation may occur after solvent removal by exposure of the coating to moisture in ambient air. With the foregoing in mind, it is a feature and advantage of the invention to provide a combination of an absorbent binder coating applied to various substrates.

BRIEF DESCRIPTION OF THE DRAWINGS

These and other objects and features of this invention will be better understood from the following detailed description taken in conjunction with the drawings, wherein.

DEFINITIONS

Within the context of this specification, each term or phrase below will include the following meaning or meanings.

"Bib area" refers to an area of a garment, typically on a front of a wearer, onto which food or beverages could potentially fall.

"Binder" includes materials that are capable of attaching themselves to a substrate or are capable of attaching other substances to a substrate.

"Breathable film" refers to a film or laminate having a water vapor transmission rate ("WVTR") of at least about 500 grams/m$^2$–24 hours, using the WVTR Test Procedure described herein. Breathable materials typically rely on molecular diffusion of vapor, or vapor passage through micropores, and are substantially liquid impermeable.

"Feminine hygiene products" include sanitary pads and napkins, as well as tampons and interlabial feminine hygiene products.

"Fluid" refers to a substance in the form of a liquid or gas at room temperature and atmospheric pressure.

"High density polyethylene (HDPE)" refers to a polyethylene having a density of about 0.95 g/cm$^3$ or greater.

"Knife over roll coating" refers to a process in which a knife is positioned, with a specified gap, above a substrate that is moving beneath the knife on a moving roll. In this manner, the knife spreads a specified thickness of coating material onto the substrate.

"Layer" when used in the singular can have the dual meaning of a single element or a plurality of elements.

"Linear low density polyethylene (LLDPE)" refers to polymers of ethylene and higher alpha-olefin comonomers such as $C_3$–$C_{12}$ comonomers, and combinations thereof, having a density of about 0.900 to 0.935 g/cm$^3$.

"Liquid-impermeable" when used to describe a layer or laminate means that liquid such as urine will not pass through the layer or laminate under ordinary use conditions in a direction generally perpendicular to the plane of the layer or laminate at the point of liquid contact.

"Liquid-permeable" refers to a layer or laminate that is not liquid-impermeable.

"Low density polyethylene (LDPE)" refers to a polyethylene having a density between about 0.91 and about 0.925 g/cm$^3$.

"Nonwoven" or "nonwoven web" refers to materials and webs or material having a structure of fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Personal care absorbent garment" includes diapers, diaper pants, training pants, swim wear, absorbent underpants, adult incontinence products, feminine hygiene products, and the like.

"Roll coating" refers to a process in which the application of a deposited material, generally as a paste, onto a substrate is carried out by transferring the deposited material from a roll onto the substrate in a more or less uniform layer using one or more rolls, which may be engraved, and a pool cylinder. A doctor blade is used to scrape any excess deposited material from the rolls or substrate. The doctor blade may be flat or have a patterned edge such as slots or ridges.

"Screen printing" refers to a method of applying a deposited material by forcing the material to be deposited through a screen that may have uniform openings or patterned openings.

"Stranded composites" refer to sheets of material to which strands of an elastomeric material are adhered to create an elastomeric composite.

"Superabsorbent" refers to a water-swellable, water-insoluble organic or inorganic material capable, under the most favorable conditions, of absorbing at least about 10 times its weight and, more desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers.

"Unit" or "polymer unit" refers to a monomer or polymer portion of a copolymer molecule or blend component that includes a different molecular structure, compared to another portion of the copolymer or blend.

"Ultra low density polyethylene (ULDPE)" refers to polymers of ethylene and higher alpha-olefin comonomers such as $C_3$–$C_{12}$ comonomers, and combinations thereof, having a density of about 0.860 to less than 0.900 g/cm$^3$.

"Wound dressing" is used interchangeably with "bandage" and "dressing," and refers to a covering to be placed over a wound.

These terms may be defined with additional language in the remaining portions of the specification.

DESCRIPTION OF PREFERRED EMBODIMENTS

This invention is directed to a combination of a crosslinkable absorbent binder coating and various substrates to which the coating is applied. The absorbent binder coating includes a hydrophilic polymer having the capability of post-application, moisture-induced crosslinking. The absorbent binder coating can provide fluid retention properties in addition to adhesive properties. Additionally, the absorbent binder coating is durable, relatively inexpensive to produce, and can be removed from surfaces and discarded after use.

In this invention, a substrate is at least partially coated with the crosslinkable absorbent binder coating, which forms an absorbent and lubricious hydrogel upon exposure to aqueous solutions. Also, upon exposure to water, the coating may release various additives, as described in greater detail below. The absorbent binder coating, particularly in a fast-drying alcohol solution, provides a convenient means of applying absorbent capacity to a wide range of surfaces. Application of the absorbent binder coating, followed by evaporation of a carrier solvent within the coating, results in formation of a coating capable of absorbing aqueous fluid or water vapor. Because the coated articles are capable of rapid absorption of water vapor, these articles are particularly suitable for humidity control products. The coating may be applied to a substrate using any suitable application process, including knife over roll coating, or roll coating, either in a continuous coverage or a discontinuous or patterned coverage. Printing applications or other suitable application techniques, including gravure printing, screen, and jet printing. The coating may also be applied to the substrate using a spray application. Suitable substrates to which the coating may be applied include, but are not limited to, nonwoven, woven, and knitted fabrics; cellulosic tissue sheets; plastic films, including polypropylene, low density polyethylene, high density polyethylene, linear low density polyethylene, and ultra low density polyethylene; Lycra stranded composites; elastomer net composites; various articles of clothing; a person's skin; non-porous surfaces; foam material; seeds; and fertilizer pellets.

Figure 1:
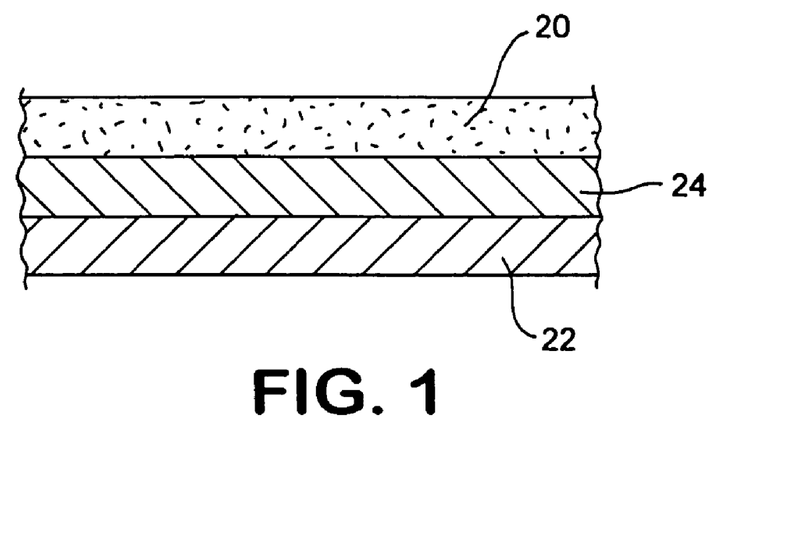
FIG. 1 illustrates an absorbent binder coating applied to a substrate with a mesh layer between the coating and the substrate.

Referring to FIGS. 1–8, the absorbent binder coating may be used as a self-applying treatment, with the coating applied directly to various substrates, such as clothing or a person's skin, to absorb sweat, spills, or other forms of wetness. The coating may be temporarily applied to such surfaces, and subsequently may be removed by peeling the coating off of the surface or washing the coating off of the surface without causing permanent damage to the underlying surface. Additionally, a mesh layer 24, such as mesh gauze, may be placed between the surface 22 and the coating 20 to facilitate peel removal, as shown in FIG. 1.

Figure 2:
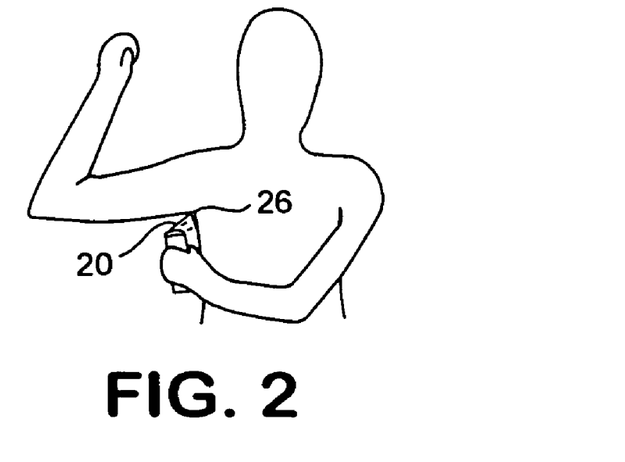
FIG. 2 illustrates a person's skin to which an absorbent binder coating is applied.
Figure 3:
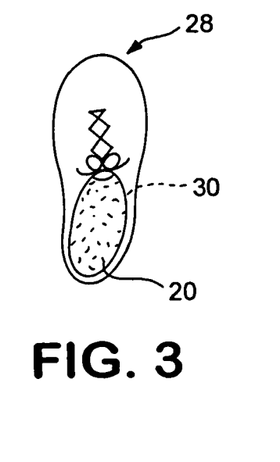
FIG. 3 illustrates a shoe to which an absorbent binder coating is applied.
Figure 4:
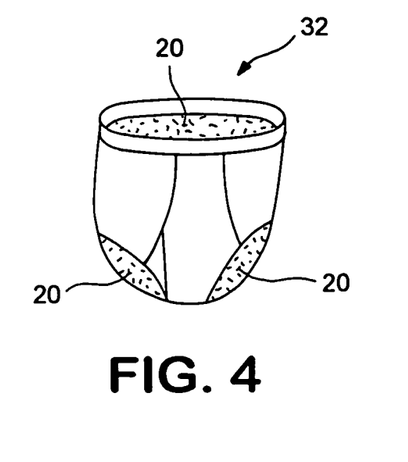
FIG. 4 illustrates an undergarment to which an absorbent binder coating is applied.
Figure 5:
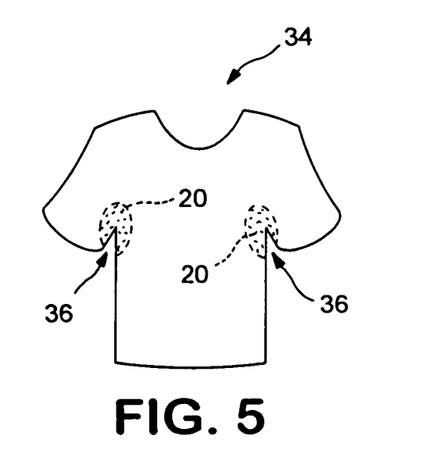
FIG. 5 illustrates a garment having an underarm area to which an absorbent binder coating is applied.
Figure 6:
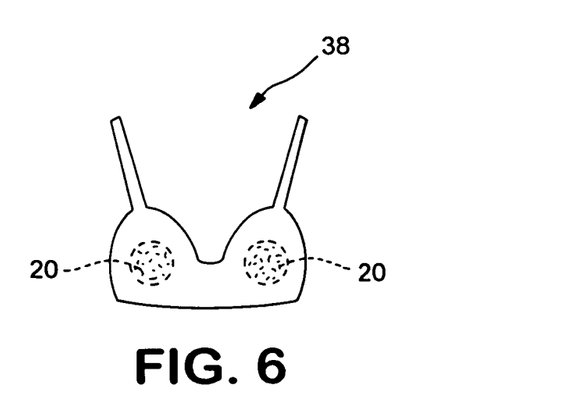
FIG. 6 illustrates a bra to which an absorbent binder coating is applied.
Figure 7:
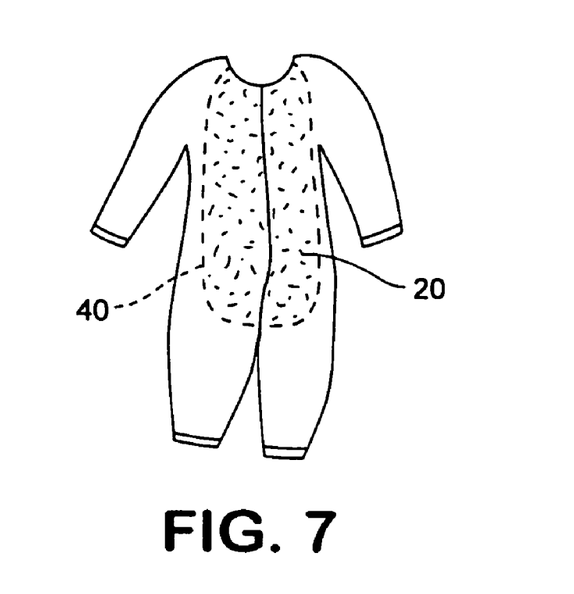
FIG. 7 illustrates a garment having a bib area to which an absorbent binder coating is applied.

As shown in FIG. 2, for example, the absorbent binder coating 20 can be applied to a person's underarm skin surface 26, in the form of a roll-on or spray application, thereby serving as an antiperspirant. Additives may be included in the coating, particularly in an alcohol solution of the coating. Such additives may include a fragrance additive, antimicrobial additive, and/or odor-absorbing particles, such as nanoparticle silica, available from Nissan Chemicals America, Houston, Tex., as 20% wt/wt aqueous suspension under the trade designation SNOWTEX-C. In this manner, the deodorant provides wetness protection from the absorbent film and odor protection from the odor-absorbing particles suspended in the absorbent film. Alternatively, or additionally, the cationic absorbent coating, as described in the Example below, may have inherent antimicrobial properties to further inhibit the generation of malodorous compounds that result from bacterial action. The absorbent binder coating may also be applied to other areas of the body including feet, back, face, or any other suitable skin surface.

As shown in FIGS. 3–8, for example, the absorbent binder coating 20 can be applied to various types of clothing such as shoes 28 or shoe inserts 30 (FIG. 3) or undergarments 32 (FIG. 4), including disposable undergarments, to provide entrapment of fluid while maintaining the comfort and fit of the clothing. Other examples of clothing to which the coating may be applied include shirts 34 and other garments having an underarm area 36 (FIG. 5) to capture sweat, bras 38 (FIG. 6) to capture milk when nursing, as well as treatment of any clothing having a bib area 40 (FIG. 7) so that the coating may serve as a spray-on or painted-on bib.

The absorbent binder coating 20 can also be applied to personal care absorbent garments, such as training pants, diapers, diaper pants, feminine hygiene products, swimwear, incontinence products, other personal care or health care garments, including medical garments, or the like. For illustrative purposes, a personal care absorbent undergarment, namely a training pant 42, is shown in FIG. 8.

Figure 8:
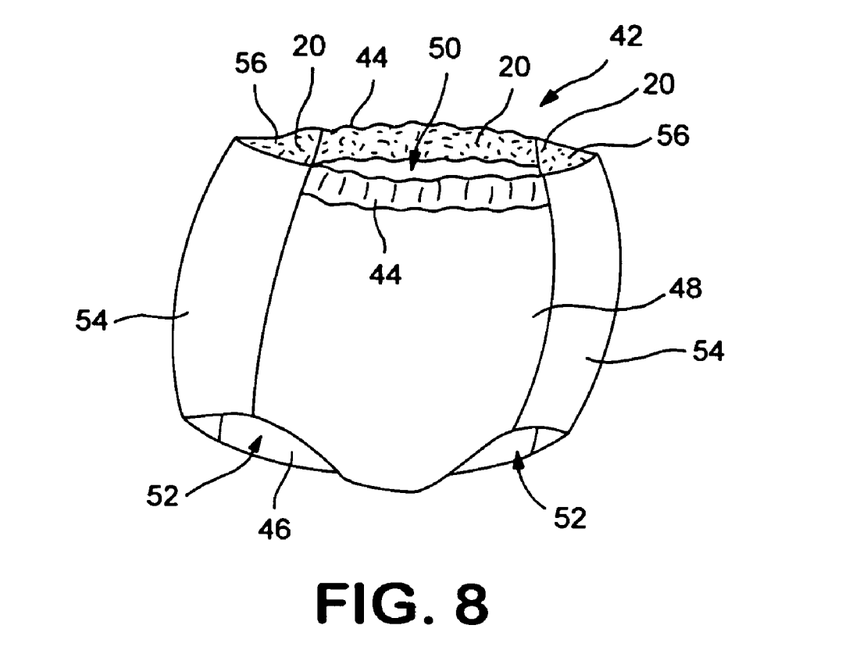
FIG. 8 illustrates a personal care absorbent garment to which an absorbent binder coating is applied.

As shown in FIG. 8, a training pant 42 having permanently bonded sides, or a training pant having refastenable sides in a fastened position, defines a three-dimensional pant configuration having a waist opening 50 and a pair of leg openings 52. The absorbent binder coating 20 can be applied to a waistband 44 of the garment around the waist opening to provide additional absorbency in the garment.

The training pant 42 includes a body side liner 46 which is configured to contact the wearer, and an outer cover 48 opposite the body side liner which is configured to contact the wearer's clothing. An absorbent assembly (not shown) is positioned or located between the outer cover 48 and the body side liner 46. Other materials that are designed primarily to receive, temporarily store, and/or transport liquid along the mutually facing surface with the absorbent assembly can also be incorporated into the absorbent article, thereby maximizing the overall absorbent capacity of the absorbent assembly, if desired. One suitable material is referred to as a surge layer (not shown) and includes a material having a basis weight of about 50 to about 120 grams per square meter (gsm), such as a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A. Another example of a suitable surge layer may include a material made of 6 denier polyethylene terephthalate (PET) and 6 denier bicomponent binder fiber, having a basis weight of about 50 to about 120 gsm. The absorbent binder coating 20 can be applied to the surge material to provide an additional reservoir for excess fluid that runs off the absorbent assembly. Discontinuous application of the absorbent binder coating 20 can be used to direct the flow of fluid to particular portions of the absorbent assembly since uncoated portions of the surge material will have a faster rate of fluid transfer than the coated portions. Conversely, coated portions of the surge material provide restriction of flow from the absorbent assembly back into the surge material, thereby inhibiting "rewet" of the body side liner 46.

The outer cover 48 desirably includes a material that is substantially liquid-impermeable, and can be elastic, stretchable or nonstretchable. The outer cover 48 can be a single layer of liquid-impermeable material, but desirably includes a multi-layered laminate structure in which at least one of the layers is liquid-impermeable. For instance, the outer cover 48 can include a vapor-permeable layer and a liquid-impermeable layer that are suitably joined together by the absorbent binder coating 20. As another example, the absorbent binder coating 20 can be used to join together the outer cover 48 and the body side liner 46. Alternatively, or additionally, the absorbent binder coating 20 can be applied to the outer cover 48 to provide a reservoir to capture any liquid run-off.

In order to forestall leakage around the leg openings 52, the garment may include a pair of containment flaps (not shown) which are configured to provide a barrier to the transverse flow of body exudates. The elasticized containment flaps define an unattached edge which assumes an upright, generally perpendicular configuration in at least a crotch region of the training pant 42 to form a seal against the wearer's body. The absorbent binder coating 20 can be applied to the flap material to further forestall leakage around the leg openings 52. Suitable constructions and arrangements for the containment flaps are generally well known to those skilled in the art and are described in U.S. Pat. No. 4,704,116 issued Nov. 3, 1987 to Enloe, which is incorporated herein by reference.

As shown in FIG. 8, the training pant 42 may include a pair of transversely opposed front side panels 54, and a pair of transversely opposed back side panels 56. The side panels 54, 56 may be integrally formed with the outer cover 48 and/or the body side liner 46, or may include two or more separate elements. Suitable materials for side panels, as well as processes of incorporating side panels into a training pant, are known and are described, for example, in U.S. Pat. No. 4,940,464 issued Jul. 10, 1990 to Van Gompel et al., which is incorporated herein by reference. In one embodiment, the absorbent binder coating 20 may be applied to an inner surface of the side panels 54, 56 to provide additional absorbency in the garment.

The absorbent binder coating can be applied to any suitable surface or combination of surfaces of the personal care absorbent garment. The coating provides for enhanced liquid absorbent capacity for a portion of the material that comes into contact with liquid. Portions of the coated material that do not come into contact with liquid are capable of absorbing water vapor which is readily released from absorbents including swollen superabsorbent and/or fluff pulp. The ability to trap excess water vapor provides for reduced relative humidity within the garment. Reduced humidity is well known to provide improved skin health.

Figure 9:
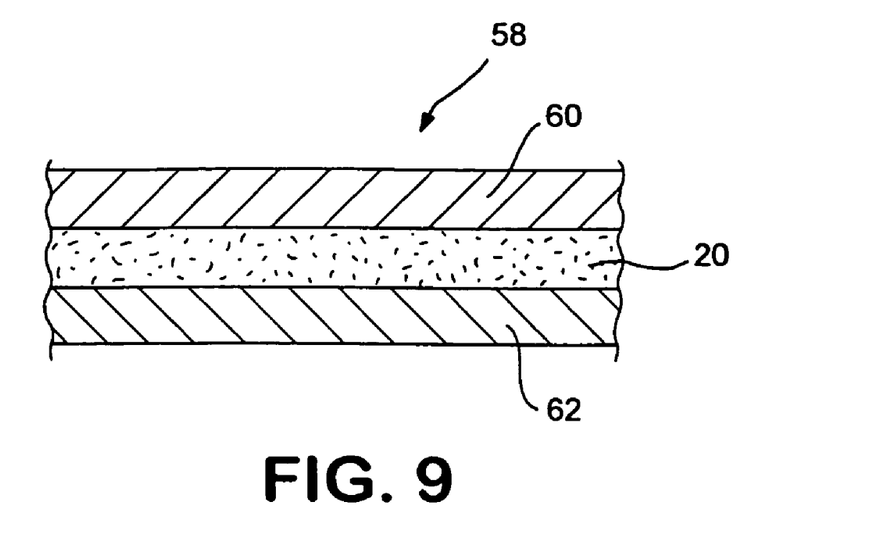
FIG. 9 illustrates a laminate including an absorbent binder coating.

In addition to forming laminates of layers within a personal care absorbent garment, other laminates 58 may also be formed with the absorbent binder coating 20. For example, the coating may be applied between a liquid-permeable substrate 60, such as a nonwoven web, and a liquid-impermeable substrate 62, such as a film, to form a laminate 58, as shown in FIG. 9. Such a laminate is particularly suitable for use in a personal care absorbent garment, as mentioned, as well as in a mattress pad. The coating between the two layers bonds the layers together as well as provides absorbency within the middle of the laminate. More particularly, the absorbent coating absorbs water vapor penetrating through a liquid-impermeable breathable film layer and traps the water vapor to prevent or reduce dampness from escaping to a liquid-permeable nonwoven web layer.

The absorbent binder coating 20 may be used as a component for use as part of a surgical drape (such as reinforcing fabric surrounding a fenestration or along an edge of a drape), and for inclusion in protective apparel, such as a surgical gown, where the nonwoven web side is positioned towards the wearer's skin while the film side is positioned away from the skin in order to absorb body perspiration or where the nonwoven faces external to the protective garment to contain fluid drips, splashes, and the like, that may otherwise run downwards and off the garment. The absorbent coating may absorb condensed water vapor between the film and the nonwoven when water vapor transmission is slowed during penetration through the liquid-impermeable film.

Figure 10:
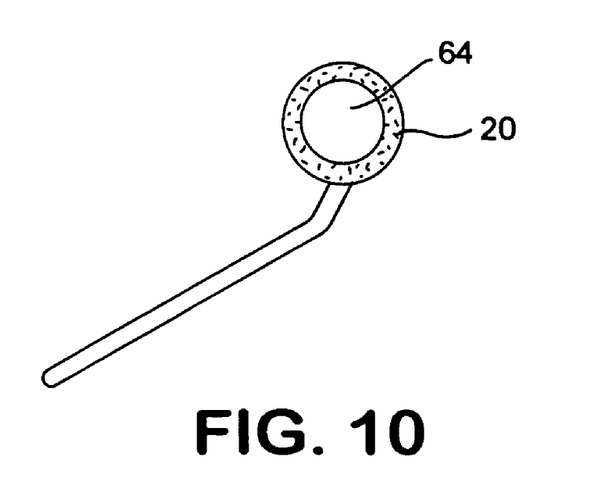
FIG. 10 illustrates a mirror to which an absorbent binder coating is applied.
Figure 11:
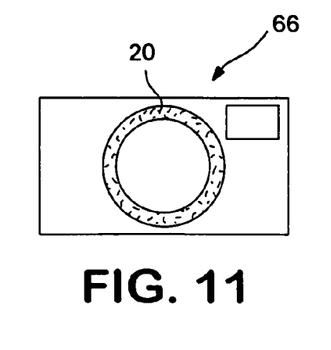
FIG. 11 illustrates a camera to which an absorbent binder coating is applied.
Figure 12:
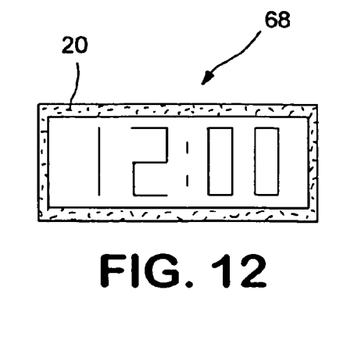
FIG. 12 illustrates a digital display to which an absorbent binder coating is applied.
Figure 13:
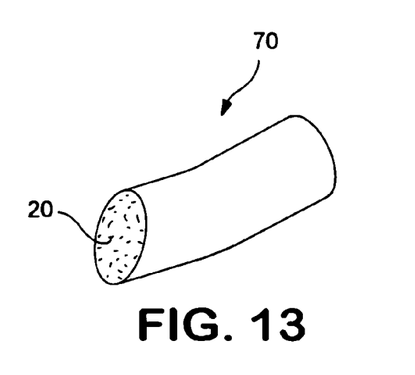
FIG. 13 illustrates a catheter to which an absorbent binder coating is applied.
Figure 14:
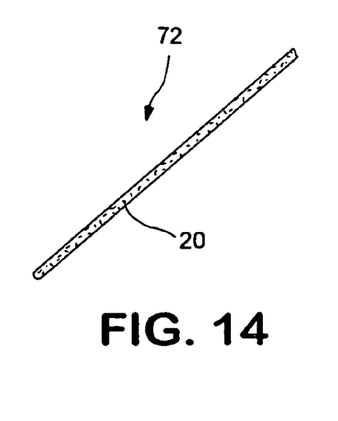
FIG. 14 illustrates a wire to which an absorbent binder coating is applied.

The absorbent binder coating 20 may also be applied to the surface of other articles, particularly those susceptible to fogging, such as mirrors 64 (FIG. 10), endoscopic cameras or other cameras 66 (FIG. 11), electronic displays 68 (FIG. 12) or other display materials, to provide a hydrophilic and absorbent surface that minimizes the formation of water droplets on the surface, thereby inhibiting fogging. Another example of a suitable application for the absorbent binder coating 20 is to a windowsill and/or window frame to prevent mold from growing due to a change in humidity during the winter. Additionally, the absorbent binder coating 20 may be applied to a catheter 70 (FIG. 13) or other medical devices, a guide wire 72 (FIG. 14), or other wire, thereby forming a lubricious coating on the object with a potential for covalent bonding to the surface. Compared to other coatings, the absorbent binder coating is applied by a low-cost process with no gamma radiation or UV treatment required.

Figure 15:
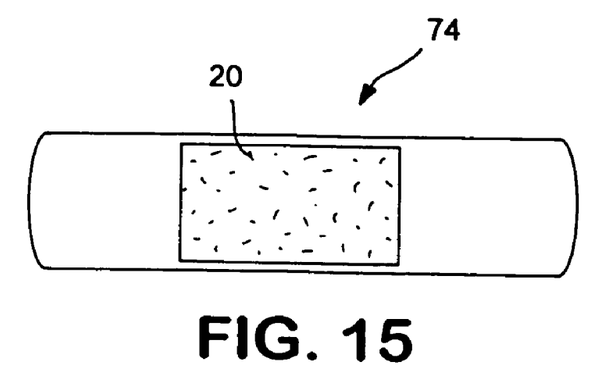
FIG. 15 illustrates a wound dressing to which an absorbent binder coating is applied.

In another embodiment, the absorbent binder coating 20 may be applied to a wound dressing 74, as shown in FIG. 15. More particularly, the coating 20 may be applied to gauze or other woven material included in the wound dressing, thereby providing absorbency and high integrity while preventing the material from adhering to any wounds. Alternatively, the wound dressing may include a nonwoven, film, and/or foam substrate to which the coating 20 is applied, resulting in a high-absorbency wound dressing that does not adhere to wounds. Another feature of the absorbent binder coating 20 is that it can act as a reservoir for releasable components that are to be delivered from the coating 20 to a region outside of the coating 20, such as, for example, a wound. In this embodiment, the coating can act to provide a controlled release of such compounds as wound healing agents, therapeutic agents, bioactive agents, antibiotics, bactericides, fungicides, drugs, growth factors, peptides, proteins, enzymes, emollients, antiseptics, anti-oxidants, wetting agents, and mixtures thereof. Suitable wound healing agents may include, for example, chitosan, niacinamide ascorbate, or the chitosan niacinamide ascorbate salt.

Figure 16:
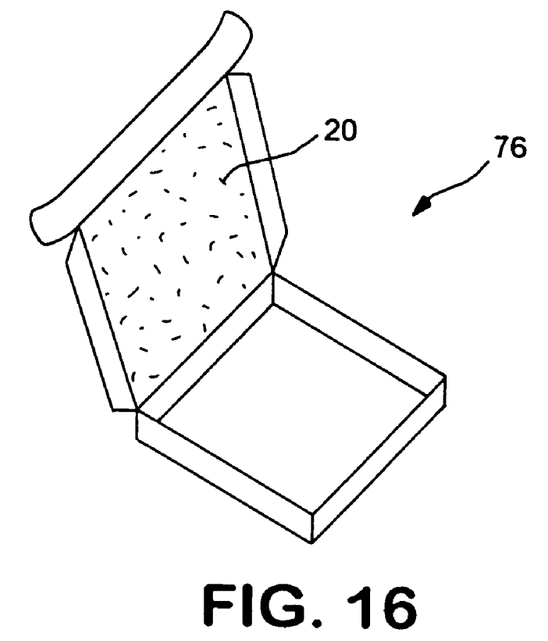
FIG. 16 illustrates a packaging material to which an absorbent binder coating is applied.

In still another embodiment, the absorbent binder coating 20 may be applied to a packaging material substrate to form a packaging material having absorbent properties. The substrate may be a plastic film, carton stock, or foam, for example. One example of a coated packaging material 76 is illustrated in FIG. 16. More particularly, the coating 20 may be applied to an inside surface of a food storage container, shipping container, or any other suitable storage container, or filler material such as bubble wrap or STYROFOAM® foam pellets, to provide a surface capable of absorbing excess water vapor into the coating. This capability prevents the release of water droplets formed from vapor condensation. Containers for take-out hot food, for example, typically trap the warm, moist air radiating from the food, causing the food to become soggy as a result of evaporation and condensation of water that accumulates on the inner surface of the container and drips into the food. The coating 20 applied to the inner surface could help keep take-out food from becoming soggy. As another example, containers for shipping produce often accumulate moisture which causes the produce to spoil. By applying the coating 20 to an inside surface of containers for shipping produce, the coated containers would have an "anti-dew" property that keeps liquid water off the produce and reduces the chances for spoilage. Similarly, the coating 20 can be applied to produce bags to maintain optimum humidity and to keep liquid water off the produce, thereby keeping the produce from getting soggy and extending the freshness.

In yet another embodiment, the absorbent binder coating 20 can be used to form various horticultural products. For example, the coating 20 can be applied to seeds to help retain seed moisture and viability. Additionally, fertilizer can be included in the coating 20, particularly in a coating polymer solution, either as a solution of fertilizer or a dispersion of fertilizer particulate. The coating 20 with the fertilizer additive can be applied to seeds to help retain seed moisture and viability, as well as to slowly release the fertilizer into a growing medium once the seeds are planted and watered.

Figure 17:
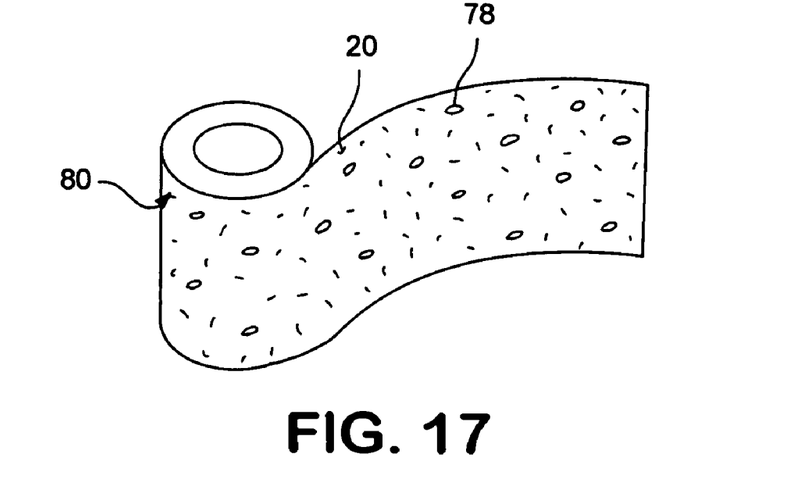
FIG. 17 illustrates a seed tape including an absorbent binder coating.

As another horticultural example, illustrated in FIG. 17, seeds 78 covered with the absorbent binder coating 20 can be applied to a fabric or tape 80 or other suitable substrate. In this manner the coating 20 also functions as an adhesive to secure the seeds 78 to the substrate 80, which allows for automated planting. Upon application of water, the seeds 78 are released from the substrate 80 and the coating 20 helps retain seed moisture and viability, while fertilizer within the coating 20, if present, is slowly released into the growing medium once the seeds 78 are watered.

The absorbent binder coating 20 may also be applied as a polymer solution to fertilizer pellets for time-released fertilization. With each watering, additional fertilizer is released into the growing medium, with the amount of fertilizer released being proportional to the amount of water applied. Alternatively, the coating solution may also function as a bonding agent to fabricate fertilizer pellets from smaller fertilizer particles.

Figure 18:
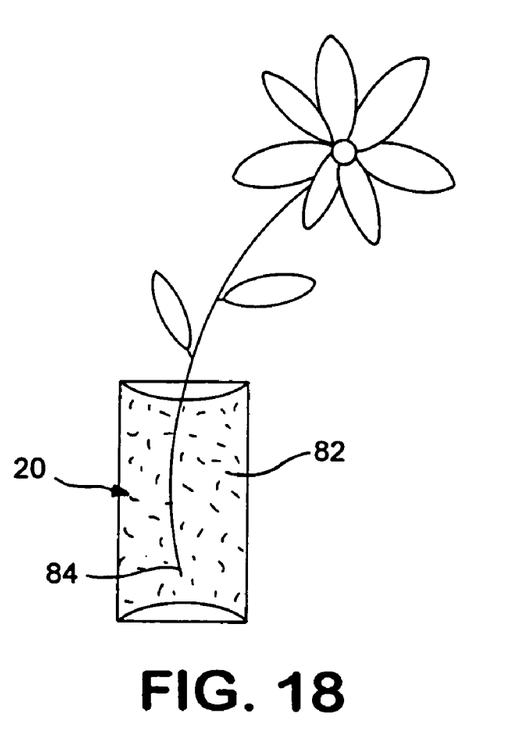
FIG. 18 illustrates a cut flower preservative including an absorbent binder.

Other additives, instead of or in addition to fertilizer, may be included in the absorbent binder coating 20. These additives may include a fungicide to combat rotting, auxin or other root growth-stimulating hormone, and/or floral preservative 82. Auxin is often applied to stem cuttings in a powder form, which is difficult to distribute in an even manner. The coating 20 including auxin, a floral preservative 82, and/or other additives, may be in a liquid or gel form to allow for uniform application to stem cuttings 84, as shown, for example, in FIG. 18. Uniform application of such additives as auxin, for example, can lead to more uniform root production for plant propagation. A mild fungicide in the coating 20 could prevent rotting of the cuttings before adventitious roots emerge.

The absorbent binder coating 20, including fungicide, fertilizer, and/or floral preservative, may be applied to freshly cut wounds on flower stems to preserve freshly cut flowers. More particularly, the coating 20 helps retain existing moisture within the stems and also distributes beneficial additives when the stems are submerged in water.

The absorbent binder coating 20 suitably includes about 15–99.8% by mass of monoethylenically unsaturated polymer units, suitably about 25–90% by mass, particularly about 30–80% by mass, or about 50–70% by mass. Suitable monoethylenically unsaturated polymer units include without limitation monoethylenically unsaturated carboxylic acid units and salts thereof, monoethylenically unsaturated sulphonic acid units and salts thereof, and monoethylenically unsaturated phosphonic acid units and salts thereof. Suitable monoethylenically unsaturated monomers that can be used to form the monoethylenically unsaturated polymer units include without limitation:

a) Carboxyl group-containing monomers including monoethylenically unsaturated mono or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid;

b) Carboxylic acid anhydride group-containing monomers, including monoethylenically unsaturated polycarboxylic acid anhydrides (such as maleic anhydride);

c) Carboxylic acid salt group-containing monomers including water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate), sodium maleate, methylamine maleate;

d) Sulfonic acid group-containing monomers, including aliphatic or aromatic vinyl sulfonic acids (such as vinylsulfonic acid, allyl sulfonic acid, vinyltoluenesulfonic acid, styrene sulfonic acid), (meth)acrylic sulfonic acids [such as sulfopropyl (meth)acrylate, 2-hydroxy-3-(meth)acryloxy propyl sulfonic acid];

e) Sulfonic acid salt group-containing monomers, including alkali metal salts, ammonium salts, amine salts of sulfonic acid group containing monomers as mentioned above; and/or f) Amide group-containing monomers, including vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth) acrylamides [such as N-methylol (meth)acrylamide, N-hydroxyethyl (meth)acrylamide], N,N-dihydroxyalkyl (meth)acrylamides [such as N,N-dihydroxyethyl (meth) acrylamide], 3-acrylamidopropyl trimethyl ammonium chloride, vinyl lactams (such as N-vinylpyrrolidone).

The absorbent binder coating 20 also includes about 0.1–20% by mass of polyacrylate ester units, such as acrylate and/or methacrylate ester units, that include an alkoxysilane functionality. The acrylate and/or methacrylate ester units are copolymerized with the monoethylenically unsaturated monomer units. In particular, the absorbent binder coating 20 may include about 0.5–15% by mass of the acrylate and/or methacrylate ester units, for instance about 1.0–10% by mass, for instance about 1.5–5.5% by mass.

The alkoxysilane functionality is a functional group or moiety that reacts with water to form a silanol group. One suitable alkoxysilane group is a trialkoxy silane group having the following structure:

wherein $R_1$, $R_2$ and $R_3$ are alkyl groups independently having from 1 to 6 carbon atoms.

The term "monomer(s)" as used herein includes monomers, oligomers, polymers, mixtures of monomers, oligomers and/or polymers, and any other reactive chemical species which is capable of co-polymerization with monoethylenically unsaturated carboxylic, sulphonic or phosphoric acid or salts thereof. Ethylenically unsaturated monomers containing a trialkoxy silane functional group are appropriate for this invention and are desired. Suitable ethylenically unsaturated monomers include acrylates and methacrylates. A particularly ethylenically unsaturated monomer containing a trialkoxy silane functional group is methacryloxypropyl trimethoxy silane, commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects are effective monomers for copolymerization in accordance with the present invention.

In addition to monomers capable of co-polymerization that contain a trialkoxy silane functional group, it is also feasible to use a monomer capable of copolymerization that can subsequently be reacted with a compound containing a trialkoxy silane functional group or a moiety that reacts with water to form a silanol group. Such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the copolymer may subsequently be reacted with, for example, but not limited to, tetramethoxysilane.

The absorbent binder coating 20 also includes about 0.1–75% by mass polyolefin glycol and/or polyolefin oxide units, suitably about 5–75% by mass, particularly about 10–60% by mass, particularly about 20–50% by mass, particularly about 30–40% by mass. The polyolefin glycol or oxide may be a glycol or oxide of an olefin polymer having about 2–4 carbon atoms. Polyethylene glycol, polyethylene oxide, polypropylene glycol and polypropylene oxide are examples of suitable polymer units. The polyolefin glycol and/or polyolefin oxide may include on average about 4 to 15,000 glycol and/or oxide units per molecule. The weight average molecular weight of polyolefin glycol units may range from about 200 to 8000. When polyolefin oxide units are employed, they may have a weight average molecular weight of about 100,000 to about 600,000.

Polyolefin glycols and polyolefin oxides are commercially available, and are common. To prepare the absorbent binder coating 20 of the invention, a pre-formed polyolefin glycol and/or oxide may be dissolved or dispersed in a reaction vessel which includes an aqueous solvent or carrier, an organic solvent or carrier such as ethanol, or a miscible combination of aqueous and organic solvent or carrier. The monomers used to form the monoethylenically unsaturated polymer units and the polyacrylate ester units are added to the solution and polymerized using a template polymerization process in which the polyolefin glycol or oxide serves as a template polymer. Before initiation, the polar groups of the monomers, for instance the acid groups of acrylic acid, are attracted to the polyolefin glycol and/or polyolefin oxide through hydrogen bonding. The steric alignment of the monomers, with the polyolefin glycol and/or oxide serving as backbone, aids in the polymerization and typically increases the chain length of the polymerizing unit. During the polymerization, radical polymerizing chains may become attached to the template polymer, resulting in grafting of polyolefin glycol and/or oxide to the copolymer being formed. However, this graft polymerization need not occur. The resulting absorbent binder coating 20 includes the polyolefin glycol and/or oxide attached to, and/or blended with, the copolymer of the monoethylenically unsaturated polymer units and the acrylate or methacrylate ester units that include the alkoxysilane functionality.

The polymerization may be initiated using a variety of methods, including without limitation thermal energy, ultraviolet light, and redox chemical reactions. A solution of the above ingredients may be added to an initiator solution at a temperature suitable for generating free radicals, for instance about 50–90° C. An initiator may be prepared by dissolving an initiator in an organic or aqueous solvent. A suitable class of initiators are organic peroxides and azo compounds, with benzoyl peroxide and azobisisobutylnitrile (ABN) as examples.

Compounds containing an O—O, S—S, or N=N bond may be used as thermal initiators. Compounds containing O—O bonds; i.e., peroxides, are commonly used as initiators for polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis(cyclohexanecarbonitrile) may be used as the initiator.

In one embodiment, the absorbent binder coating 20 is made by combining a first aqueous monomer solution including a reducing polymerization initiator with a second aqueous monomer solution including an oxidizing polymerization initiator, wherein the initiators react to form a binder coating. The first aqueous monomer solution further includes a monoethylenically unsaturated monomer and an ethylenically unsaturated monomer that contains an alkoxysilane functionality. The second aqueous monomer solution includes a monoethylenically unsaturated monomer. One or both solutions may include the polyolefin glycol and/or polyolefin oxide template polymer. Suitably, the binder coating is formed in about 100 minutes or less, or 60 minutes or less, desirably in about 30 minutes or less, or about 15 minutes or less, or about 10 minutes or less.

The pH of the first and/or second aqueous monomer solution is adjusted to about 4.5 to 8, suitably about 5.5 to about 7.0. The pH of the first aqueous solution may be adjusted prior to the addition of the ethylenically unsaturated monomer. Desirably, the pH of the first aqueous monomer solution is adjusted prior to the addition of the reducing polymerization initiator. The pH of the second aqueous solution may be adjusted prior to the addition of the oxidizing polymerization initiator. Alternatively, the pH of the combined first and second aqueous monomer solutions may be adjusted to about 4.5 to 8, suitably about 5.5 to about 7.0. If desired, the pH may be increased after polymerization is complete, by addition of a suitable basic solution. The extent of neutralization can be used to adjust the properties of the coating. Greater neutralization of the acid functional components generally provides for greater absorbent capacity, while adhesiveness is generally enhanced with more acid functionality.

The amounts of the polymerization ingredients added to the first and second aqueous solutions are selected so as to produce the absorbent binder coating 20 having the coating described above.

In one embodiment, a surfactant may be added to the first and/or second aqueous monomer solution to disperse the ethylenically unsaturated monomer. One surfactant suitable for use in the present invention is a dioctyl sodium sulfosuccinate available under the trademark AEROSOL OT from Cytec Industries, Inc. of Paterson, N.J.

The first aqueous monomer solution further includes a reducing polymerization initiator. Suitable reducing polymerization initiators include, but are not limited to, ascorbic acid, alkali metal sulfites, alkali metal bisulfites, ammonium sulfite, ammonium bisulfite, alkali metal hydrogen sulfite, ferrous metal salts such as ferrous sulfates, sugars, aldehydes, primary and secondary alcohols, and combinations thereof. In one embodiment, the reducing polymerization initiator includes ascorbic acid.

The second aqueous monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one embodiment, the oxidizing polymerization initiator includes hydrogen peroxide.

Generally, when the first aqueous monomer solution is combined with the second aqueous monomer solution the reducing polymerization initiator reacts with the oxidizing polymerization initiator, e.g. a redox reaction, thereby initiating a polymerization reaction to form a binder coating including a monoethylenically unsaturated monomer and an ethylenically unsaturated monomer that has post-application, moisture-induced crosslinking capability.

The absorbent binder coating 20 may be applied to a substrate and subsequently dried to form a cast film. Once the absorbent binder coating 20 is applied to the substrate, crosslinking can be moisture-induced by hydrolysis and condensation of alkoxysilanes. For example, crosslinking of the absorbent binder coating 20 can be induced by concentrating the absorbent binder coating 20 on the substrate through the removal of the water to promote condensation of silanols generated by hydrolysis of alkoxysilanes. Typically, crosslinking begins at a solution concentration above about 30 percent by weight absorbent binder coating 20. Furthermore, if the substrate material has hydroxyl group functionality on the surface, then the silanols within the absorbent binder coating 20 may react with the hydroxyl to form a covalent bond between the absorbent binder coating 20 and the hydroxyl-containing surface. Non-limiting examples of substrates with hydroxyl surface functionality include glass, sand, or cellulose.

Alternatively, the resulting absorbent binder coating 20 may be applied to a substrate, such as for the purpose of adhering various components of an absorbent product to one another during the manufacturing process of absorbent products. In another embodiment, the absorbent binder coating 20 may be applied to a substrate as a coating by itself, thereby serving as an absorbency additive. In either of these embodiments, the absorbent binder coating 20 is suitably present in any concentration that provides a viscosity suitable for the application process. The absorbent binder coating 20 may be applied to the substrate using any suitable application process, including knife over roll coating, or roll coating, either in a continuous coverage or a patterned coverage. Printing applications are other suitable application techniques, including gravure printing, screen, and jet printing. The absorbent binder coating 20 may also be applied to the substrate using a spray application.

In another embodiment, the absorbent binder coating 20 may be prepared using a continuous process wherein the polymerization and/or neutralization reaction is carried out in a suitable reactor that conveys the resulting binder coating, upon completion of the polymerization reaction, directly to an apparatus for applying the absorbent binder coating 20 onto the substrate. Such a continuous process may be desirable where conditions, such as high heat, may cause premature crosslinking of the binder coating that would hinder application of the absorbent binder coating 20 onto the substrate.

One advantage of the absorbent binder coating 20 of the invention is that it provides a water-soluble ionic polymer capable of crosslinking without radiation, within about 10 minutes, at a temperature less than about 120° C. Eliminating the need for radiative crosslinking provides a significant processing advantage. The crosslinking at temperatures less than about 120° C., suitably less than about 100° C., permits the absorbent binder coating 20 to be applied to a substrate such as an absorbent article, and then crosslinked without degrading or damaging the substrate. The crosslinking occurs within about 10 minutes, suitably within about 8 minutes, particularly within about 6 minutes provides an efficient, commercially feasible, cost-effective crosslinking process. Furthermore, the coating 20 can be formulated to provide a dry surface that has varying degrees of surface tack. The ionic polymer may bear a positive charge, a negative charge, or a combination of both, and should have an ionic unit content of at least 15 mole percent. The ionic polymer may include a variety of monomer units described above, and suitably contains a carboxyl group-containing unit or a quaternary ammonium-containing unit.

EXAMPLE

The absorbent binder coating is capable of absorbing water vapor, at 22° C. and 50% relative humidity, at a rate of at least 4 weight percent per hour. Under similar conditions particulate superabsorbent absorbs water vapor at a rate of about 0.2% per hour. The rapid rate of absorbance and the capability to form coatings with the absorbent binder coating make these materials particularly suitable for humidity control products.

The coating was prepared as follows. Two monomer solutions were prepared separately. Solution No. 1 was prepared as follows. To 55.0 grams of a 75% solution of (3-acrylamidopropyl) trimethyl ammonium chloride (0.20 moles) was added 21.3 grams of deionized water, 6.0 grams of PEG 200 (molecular weight 200). Then, 0.18 grams ($1.02 \times 10^{-3}$ moles) of ascorbic acid was added to the solution. This mixture was stirred with a magnetic stir bar at about 60 rpm in a bath of water at about 23° C. until the ascorbic acid was dissolved and the mixture cooled to 23° C.

Solution No. 2 was prepared in the following manner. To 55.0 grams of a 75% solution of (3-acrylamidopropyl) trimethyl ammonium chloride (0.20 moles) was added 21.3 grams of deionized water, 6.0 grams of PEG 200 (molecular weight 200), 0.37 ml of 30% aqueous hydrogen peroxide and 1.0 ml ($5.42 \times 10^{-3}$ moles) of 3-(trimethoxysilyl)propyl methacrylate. This mixture was stirred with a magnetic stir bar at about 60 rpm in a bath of water at about 23° C. to provide a clear solution cooled to 23° C.

Solution No. 2 was added to Solution No. 1 while stirring with a magnetic stir bar. A thermocouple was used to monitor the temperature and observe the reaction exotherm. No polymerization exotherm was evident so the mixture was placed into a water bath and the temperature was raised to 70° C. over a time period of 35 minutes. An exotherm was evident by a rise in temperature to 73° C. over a period of 1 minute and the solution became highly viscous. The reaction beaker was removed from the water bath after 50 minutes from the addition of Solution No. 2 to Solution No. 1. 152 grams of deionized water was added to reduce the polymer concentration to about 33%.

To 50 grams of the 33% polymer solution was added 2.5 ml of a 0.2% solution of hydrochloric acid. This solution was poured into two weighing dishes (100 cm² area) and the solution was dried for two days in the laboratory hood. The resultant film was very soft and flexible and slightly tacky. A portion of the film was cut off (0.5 gram) and soaked in 20 ml of 0.9% saline for 60 minutes. The film swelled substantially and absorbed about 12000% of the dry weight of the film.

The remainder of the film (3.806 gram) was placed in a climate-controlled room at 22° C. and 50% relative humidity. After two hours in these conditions the film was reweighed and was found to weigh 4.229 grams. The increase in weight of 0.423 grams is an increase of 11.1% in two hours or about 5.6% per hour.

While the embodiments of the invention disclosed herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. A combination of an absorbent binder coating and a substrate, the combination comprising:
    an absorbent binder coating at least partially covering a substrate, wherein the absorbent binder coating includes a reaction product of about 15–99.8% by mass of monoethylenically unsaturated units; about 0.1–20% by mass polyacrylate ester units that include an alkoxysilane functionality; and about 0.1–75% by mass polymer units selected from polyolefin glycol units, polyolefin oxide units, or combinations thereof;
    wherein the reaction product includes a copolymer of at least the monoethylenically unsaturated units and the polyacrylate ester units;
    the copolymer establishes intimate contact with the substrate;
    the copolymer crosslinks after establishing intimate contact with the substrate;
    the copolymer assumes a final shape on the substrate to form the coating; and
    the coating absorbs water vapor at 22° C. and 50% relative humidity at a rate of at least 4 weight percent per hour, for at least two hours.

2. The combination of claim 1, further comprising a mesh layer between the absorbent binder coating and the substrate.

3. The combination of claim 1, wherein the substrate comprises a person's skin.

4. The combination of claim 3, wherein the combination comprises an antiperspirant.

5. The combination of claim 1, wherein the substrate comprises an article of clothing.

6. The combination of claim 5, wherein the article of clothing is selected from the group consisting of a garment having an underarm area, a bra, a garment having a bib area, an undergarment, a disposable undergarment, a shoe, and a shoe insert.

7. An absorbent article comprising the combination of claim 1, wherein the substrate includes at least one of the group consisting of surge material, flap material, outer cover material, waistband material, and side panels.

8. The combination of claim 1, wherein the absorbent binder coating further comprises at least one of the group consisting of a fragrance additive, odor-absorbing particles, and an antimicrobial additive.

9. The combination of claim 1, wherein the substrate comprises at least one of the group consisting of a mirror, a camera, an electronic display, a windowsill, and a window frame.

10. The combination of claim 1, wherein the substrate comprises at least one of the group consisting of a catheter and a wire.

11. A wound dressing comprising the combination of claim 1.

12. The wound dressing of claim 11, wherein the substrate comprises at least one of the group consisting of a woven material, a nonwoven material, a foam material, and a film.

13. The wound dressing of claim 11, wherein the absorbent binder coating further comprises a wound healing agent.

14. The combination of claim 1, wherein the substrate comprises a liquid-permeable material on a first side of the absorbent binder coating.

15. The combination of claim 14, further comprising a liquid-impermeable, vapor permeable material on a second side of the absorbent binder coating.

16. A mattress pad comprising the combination of claim 15.

17. A personal care absorbent garment comprising the combination of claim 15.

18. The absorbent garment of claim 17, wherein an outer cover of the absorbent garment comprises the combination.

19. A medical garment comprising the combination of claim 15.

20. A surgical drape comprising the combination of claim 15.

21. The combination of claim 15, wherein the liquid-permeable layer comprises a nonwoven web.

22. The combination of claim 15, wherein the liquid-impermeable layer comprises a breathable film.

23. The combination of claim 1, wherein the substrate comprises a plastic film.

24. The combination of claim 1, wherein the substrate comprises carton stock.

25. The combination of claim 1, wherein the substrate comprises a foam.

26. The combination of claim 1, wherein the substrate comprises a food storage container.

27. The combination of claim 1, wherein the substrate comprises a produce storage bag.

28. The combination of claim 1, wherein the substrate comprises a shipping container.

29. The combination of claim 1, wherein the substrate comprises a fertilizer.

30. The combination of claim 1, wherein the substrate comprises a plurality of fertilizer pellets.

31. The combination of claim 1, wherein the substrate comprises one or more seeds.

32. The combination of claim 1, comprising a fungicide.

33. The combination of claim 1, comprising a floral preservative.

* * * * *